United States Patent [19]
Zablotsky et al.

[11] Patent Number: 5,738,624
[45] Date of Patent: Apr. 14, 1998

[54] MASK FOR APPLYING A MAGNETIC FLUX FIELD TO FACIAL SKIN

[76] Inventors: Charles Zablotsky, 5821 Quiet Oak La., Fort Lauderdale, Fla. 33312; Theodore J. Zablotsky, 44 Miamis Rd., West Hartford, Conn. 06117

[21] Appl. No.: 292,697

[22] Filed: Aug. 18, 1994

Related U.S. Application Data

[63] Continuation of Ser. No. 75,723, Jun. 14, 1993, abandoned.

[51] Int. Cl.⁶ ................................................. A61N 2/00
[52] U.S. Cl. ....................................... 600/9; 600/15
[58] Field of Search ................................ 600/9–15

[56] References Cited

U.S. PATENT DOCUMENTS

| | | | |
|---|---|---|---|
| 4,489,711 | 12/1984 | Latzke | 128/1.3 |
| 4,549,532 | 10/1985 | Baermann | 128/1.3 |

FOREIGN PATENT DOCUMENTS

| | | | |
|---|---|---|---|
| 2575926 | 7/1986 | France | 600/15 |
| 2583292 | 12/1986 | France | |
| 2591495 | 6/1987 | France | |
| 2733982 | 2/1979 | Germany | 600/15 |
| 0839555 | 6/1981 | U.S.S.R. | 600/15 |
| 2242362 | 10/1991 | United Kingdom | 600/15 |

OTHER PUBLICATIONS

Lin et al, "Geophysical Variables and Behavior XXVII Magnetic Necklace . . . " Apr. 1985, pp. 639–649.
Stratznigg, Field Study of the Application of Static–Magnetic Fields in Human Medicine, Mar. 1984.
Lin et al, Geophysical Variables and Behavior. Magnetic Necklace.

*Primary Examiner*—John P. Lacyk
*Attorney, Agent, or Firm*—Dickinson, Wright, Moon, Van Dusen & Freeman

[57] ABSTRACT

A face mask for applying a magnetic flux field to the face of a human being comprises sheets of flexible plastic material joined together to provide a pocket therebetween containing a formable material by which the mask is adapted to conform to the contour of the face of person wearing the mask. The formable material can be a viscous liquid or thermoplastic material, and the mask is provided with permanent magnet sheet elements which overlie forehead, temple, cheek and mouth areas of the face and are urged to lie parallel thereto by the deformable material.

19 Claims, 3 Drawing Sheets

5,738,624

MASK FOR APPLYING A MAGNETIC FLUX FIELD TO FACIAL SKIN

This application is a continuation of application Ser. No. 075,723 filed Jun. 14, 1993, now abandoned.

BACKGROUND OF THE INVENTION

The present invention relates to the art of therapeutic devices and, more particularly, to a face mask for applying a magnetic flux field to wrinkled skin portions of the face of a human being.

Flexible, permanently magnetized sheets have been used in the past for therapeutic purposes including, for example, promoting blood circulation and alleviating pain. Examples of such magnetic sheet material devices are shown, for example, in U.S. Pat. Nos. 4,489,711 to Latzke and 4,549,532 to Baermann. Generally, the sheet material is a flexible synthetic material which is compatible with the skin and which has permanent magnetic particles of ferrite material embedded therein and magnetized to provide alternating positive and negative areas which are operable to establish magnetic fields which pass through underlying portions of the body of a human being when the sheet material is applied thereto. The provision of a molded face mask with magnets positioned thereon to apply magnetic flux fields to wrinkled facial areas of a human being is disclosed in French patents 2,583,292 and 2,591,495.

In connection with magnetic therapy, it is desirable to orient the magnetic sheet on the body of a person so that the magnetic field lines are in a particular orientation relative thereto. Accordingly, with magnetic sheet material in which the alternating positive and negative areas are linear, or linear and parallel to one another, such as in the French patents and the patent to Latzke, it is difficult to assure that the magnetic sheet material is properly oriented relative to the body of the user to obtain the desired direction for the lines of flux. However, as disclosed in the aforementioned patent to Baermann, the alternating positive and negative areas can be arranged relative to one another on the sheet material to establish magnetic fields having angularities with respect to a line traversing the sheet material. Therefore, the direction of the lines of flux is universal, thus optimizing obtaining proper orientation of the flux fields and avoiding the uncertainty of such orientation when using magnetic sheet material having linear or linear and parallel areas of magnetization.

SUMMARY OF THE INVENTION

In accordance with the present invention, an improved face mask is provided incorporating magnetic sheet material of the foregoing character, and preferably magnetic sheet material having alternating positive and negative areas angularly related as disclosed in the Baermann patent, for applying on skin portions of the face of a human being. The skin portions include the forehead, areas under the eyes and adjacent the nose, areas surrounding the mouth, cheek and jaw areas, and the temple areas laterally adjacent the eyes. It is known that facial wrinkles are caused by gradual changes in the nature of the fibrous and elastic elements that keep the human skin supple and smooth. Other than in connection with the normal aging process, it is not known what causes the changes in the nature of the fibrous and elastic elements of the skin, but it is of course well known that numerous people categorized as being young have facial wrinkles and that numerous creams, ointments and other medications are available for application to wrinkled skin areas of the face to promote a reduction in or stabilization against worsening of the wrinkles in these areas.

In connection with applying magnetic flux field therapy to wrinkled skin portions of a person's face in accordance with my invention, magnetic sheet material of the foregoing character can be cut to provide pieces of size and/or contour corresponding to the areas to be treated, or the sheet material can be produced with pre-contoured profiles particularly suited for different face portions.

The magnet pieces are supported on a face mask which is readily deformable to conform to the contour of the face of a person wearing the mask. Therefore, the same mask can be used by different people, thus avoiding the cost of molding a mask for each different face contour, or reducing the efficiency resulting from a lack of conformity of a given mask with different facial contours. Preferably, the mask is in the form of an envelope of flexible material containing a filling of a viscous liquid gel, or a thermoplastic material, which enables the mask to be readily formed to the contour of a wearer's face and to position the magnetic sheets adjacent and parallel to the facial skin therebeneath. By using magnetic material in which the alternate positive and negative areas are angularly related relative to a line traversing the surface of the magnetic sheet material, care with respect to the orientation of the magnetic sheet material relative to the wrinkled face portions is minimized. In this respect, lines of wrinkles in certain face portions are neither linear nor parallel, whereby the wrinkles as well as blood vessels underlying the skin will traverse areas of alternating polarity in any given orientation of the magnetic sheet material relative thereto. It is contemplated that the primary time for application of the mask to the user's face would be at night time so that the therapy takes place while the person is sleeping, although it will be obvious that the therapy can be employed at any time suitable to the person and in connection with other therapies at a specialized location such as a health spa. By supporting the pieces of magnetic material on a formable face mask worn by the user, positioning of the magnet pieces adjacent the skin of the wearer is optimized, thus to promote comfort to the wearer and the desired direction of the magnetic field relative to the skin.

It is also believed that the application of magnetic fields to portions of the face in accordance with the present invention, and especially facial areas surrounding the eyes, promotes improvement with regard to certain eyesight problems by increasing blood circulation in specific areas of tissue. More particularly in this respect, it is known that permanent magnet magnetic fields provide for a hyperemic state in which there is an increased amount of blood in a specific area of tissue. Providing increased blood flow to an area of tissue will increase the nutrient concentration and will act to ameliorate inflammatory conditions and provide for various musculoskeletal effects.

The lens of the eye, like the cornea, serves to converge rays of light on the retina. The cornea actually has twice the refractive power of the lens, but the lens has variable focusing power allowing the eye to focus on near or distant objects. The ability to focus is dependent upon the relaxation and contraction of the circular ciliary muscle which tightens and loosens fibers which control the shape of the lens. The ciliary muscle is composed of linear fibers and circular fibers and lies between the corneoscleral junction and ciliary process. During contraction, the ciliary muscle acts to pull the ciliary body forward which relieves the tension on the suspensory ligament of the lens. This causes the elastic lens to become more convex, thus increasing the refractive power of the lens. When the muscle is in its most relaxed state and the pull on the ligaments is still too strong to allow the lens to relax, accommodation is affected and the condition of myopia or "near sightedness" results. The opposite effect, when the ciliary muscle is in it maximum state of contraction and there still is not enough tension on the ligaments to sufficiently bend the lens, is "far sightedness" or hyperopia. Changing the shape of the eye by even one millimeter can cause a change in one's prescription by as much as three diopters, so even a small difference in the state of relaxation of the of the ciliary muscles could dramatically alter one's vision, especially one's ability to focus on distant objects. There is also the issue of the lens itself with respect to aging. As one ages, the lens becomes less flexible due to a change in the balance of the composition of the lens and the electrolyte water pump which controls the hydration level of the lens. As one ages, the normal concentrations of protein, glutathione and calcium changes due to the decrease in water content. The calcium concentration increases and the protein becomes more insoluble. As the process continues, the lens becomes increasingly hard and accommodation is affected.

It is accordingly an outstanding object of the present invention to provide an improved face mask supporting permanent magnet elements for applying a magnetic flux field to a wrinkled skin portion of the face of a human being to promote blood circulation.

Another object is the provision of a face mask supporting permanent magnet elements for applying magnetic flux fields to portions of the face of a human being surrounding the eyes to promote blood circulation to the ciliary muscles situated at the front of the eyes and to promote the flow of fluid in the eye lenses.

A further object is the provision of a face mask of the foregoing character which is readily formable to the contour of the face of a person wearing the mask.

Yet a further object is the provision of a face mask of the foregoing character which can be used by persons having different facial contours with the same degree of conformity of the mask to the contour of each persons face and with the same efficiency with respect to positioning the magnet sheets relative to the underlying face surface.

Another object is the provision of a face mask of the foregoing character which optimizes the directional relationship between the magnetic field lines and facial wrinkles and between the magnetic field lines and blood vessels, tissue and the like underlying the skin.

BRIEF DESCRIPTION OF THE DRAWING

The foregoing objects, and others, will in part be obvious and in part pointed out more fully hereinafter in conjunction with the written description of preferred embodiments of the present invention shown in the accompanying drawings in which.

DESCRIPTION OF PREFERRED EMBODIMENTS

Figure 1:
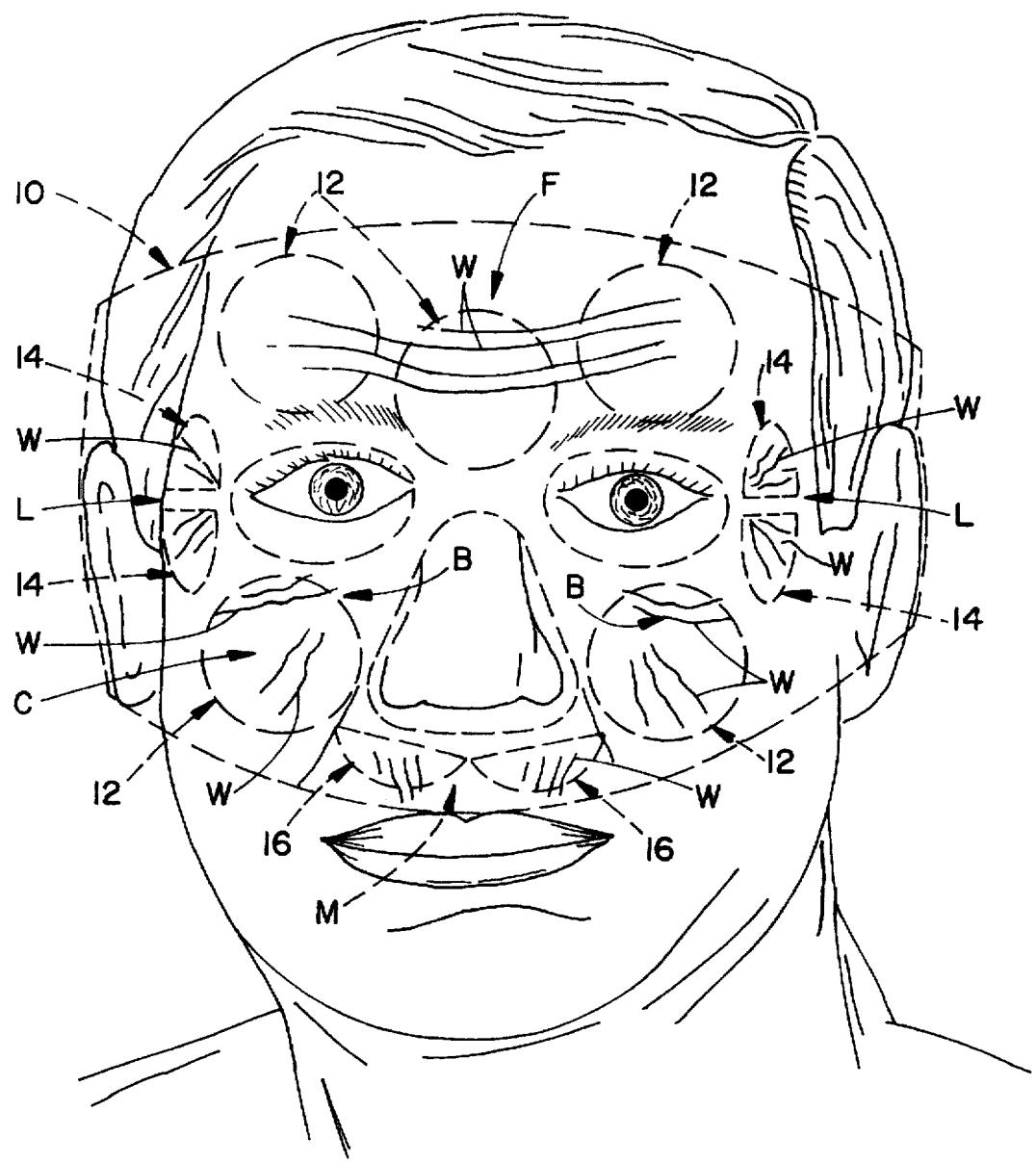
FIG. 1 is an illustration of a human face having wrinkled skin portions and schematically illustrating a face mask thereon having sheets of magnetic material for applying magnetic flux fields to the wrinkled skin portions and about the eyes in accordance with the present invention.

Referring now in greater detail to the drawings wherein the showings are for the purpose of illustrating preferred embodiments of the present invention, and not for the purpose of limiting the invention, FIG. 1 illustrates the face of a human being and wrinkled portions thereof to which a magnetic flux field is applied through the use of a face mask in accordance with the present invention to promote blood circulation. More particularly, the face is shown as having wrinkles in a forehead portion F, in the temple areas L laterally outwardly of the eyes, in areas B below the eyes, in cheek areas C, and in the area M above the mouth. Further, as described in greater detail hereinafter, FIG. 1 schematically illustrates a face mask 10 carrying a plurality of magnetic sheets overlying the wrinkled face portions, namely circular sheet 12 overlying the forehead portion F immediately above the eyes and overlying cheek areas C and areas B beneath the eyes, semi-circular sheets 14 overlying the temple areas L outwardly of the eyes, and sheets 16 of circular segment contour overlying mouth area M. As will become apparent hereinafter, each of the sheets 14 and 16 is a segment of circular sheet 10.

Figure 2:
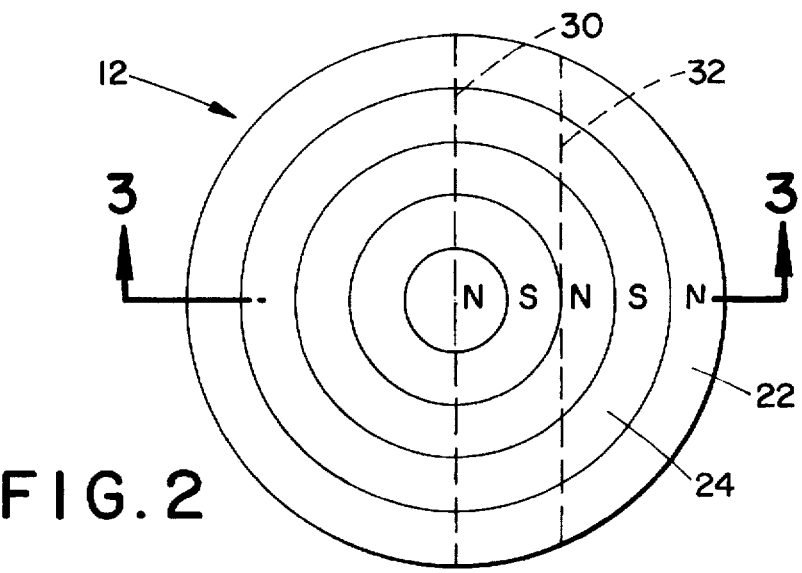
FIG. 2 is a plan view of a preferred flexible magnetic sheet for the face mask.

Magnetic sheets 12 are preferably flexible and formed of a suitable rubber-like synthetic material which is compatible with the skin and in which permanent magnetic particles are embedded in a well known manner and, preferably, adjacent one surface of the sheet material. The particles may, for example, comprise barium ferrite or strontium ferrite, and the thickness of the sheet material is such that the sheet remains flexible in use while generally comfortable to the user when applied to the surface to be treated. At the same time, the thickness should be such that sufficient particles may be embedded therein to assure a desired magnetic field flux density. Preferably, the sheet material has a thickness of from about 0.5 mm to about 3.0 mm, and the magnetic particles are sufficient to provide a flux density of from about 50 to 1,000 Gauss. As shown in detail in FIGS. 2 and 3 of the drawing sheet magnet 12 is circular and comprises a sheet 18 of flexible, rubber-like thermoplastic material having an active surface 20 intended to face the skin in the corresponding area of the face. The magnetic particles are embedded in the active surface and are selectively magnetized in a known manner to establish a plurality of concentric rings providing alternating north poles 22 and south poles 24 which may be of the same or different widths radially of the sheet. The direction of the magnetic field lines between adjacent poles is represented by the curved broken lines 26 in FIG. 3. Preferably, active surface 20 is provided with a thin layer of fabric 28 to promote comfort for a person wearing the mask. The circular configuration and concentric magnetic pattern of magnetic sheet 12 advantageously provides for wrinkles and blood vessels underlying the skin to be traversed by the lines of flux which extend radially and circumferentially of sheet 12, regardless of the angular orientation of the plane of magnetic sheet 12 relative to the face area. As will be appreciated from FIG. 2, magnet sheets 14 and 16 are obtained by cutting a magnet sheet 12 respectively along a diametrical line 30 or a segment line 32.

Figures 5, 6:
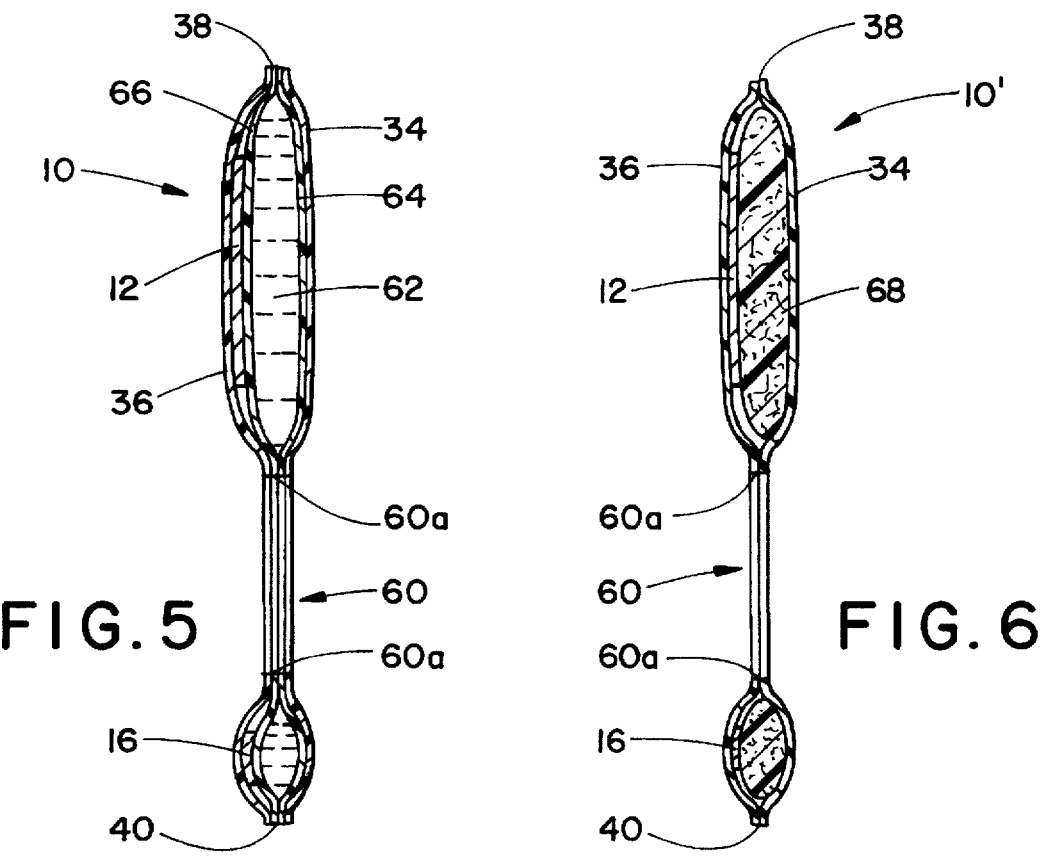
FIG. 5 is a sectional elevation view of the face mask taken along line 5—5 in FIG. 4.
FIG. 6 is a sectional elevation view similar to FIG. 5 and illustrating a further embodiment of a face mask according to the invention.
Figure 4:
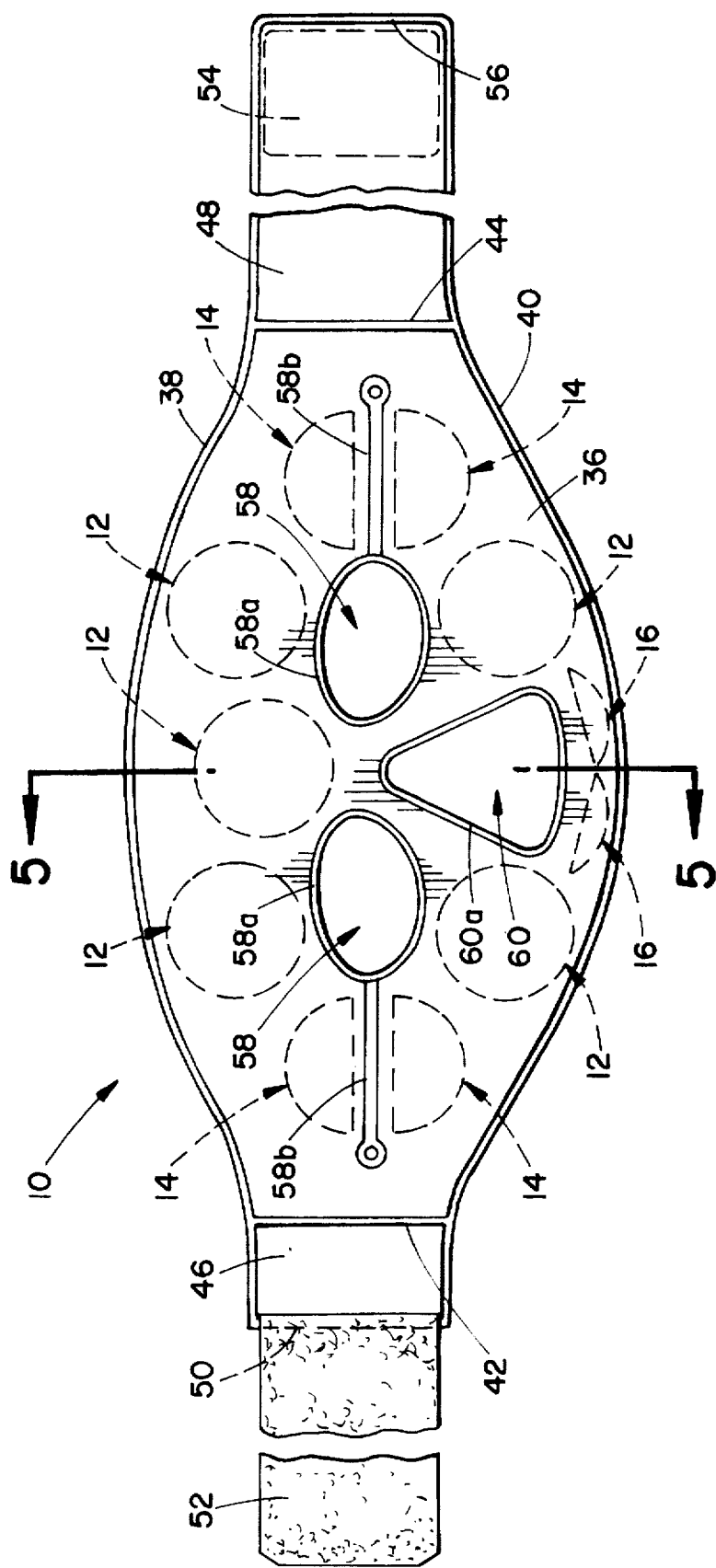
FIG. 4 is a plan view of a face mask in accordance with the invention.

One embodiment of face mask 10 in accordance with the present invention is illustrated in FIGS. 4 and 5 of the drawing. As shown in the latter figures, face mask 10 is comprised of front and back sheets 34 and 36, respectively, preferably of a hypo-allergenic vinyl material heat sealed or otherwise joined to provide the face mask with a peripheral edge including top edge portion 38, bottom edge portion 40 and end portions 42 and 44. Preferably, the front and back sheets extend outwardly from end edge portions 42 and 44 to provide straps 46 and 48, respectively, which extend about a persons head so as to removably hold the mask in place against a person's face. More particularly in this respect, the front and back sheets in the area of each strap portion are peripherally joined together such as by heat sealing, the outermost end 50 of the strap 46 has one component 52 of a VELCRO brand fastener arrangement heat sealed thereto, and strap 48 has the second component 54 of the VELCRO brand fastener arrangement heat sealed or otherwise secured thereto inwardly of the outermost end 56 of the strap. Preferably, front and back sheets 34 and 36 are apertured to provide eye openings 58 and nose opening 60, and the front and back sheets are peripherally heat sealed thereabout as indicated by the numerals 58a and 60a. It is likewise preferred to heat seal the front and back sheets along linear lines 58b extending outwardly from the outer ends of eye openings 58, for the purpose set forth hereinafter.

Front and back sheets 34 and 36, when heat sealed in the foregoing manner, provide a pocket therebetween and within the outer peripheral thereof as defined by edge and end portions 38, 40, 42 and 44. In accordance with the present invention, this pocket is provided with a filling which promotes conformity of the side of the mask facing a person's face with the contour of the face portion covered by the mask and, therefore, as will become apparent hereinafter, a desired positioning of the magnet sheets parallel to the facial skin of a person wearing the mask so as to optimize the direction of the magnetic fields relative to the wearer's skin. In the embodiment shown in FIGS. 4 and 5, the filling is a liquid 62 which, preferably, is enclosed in a vinyl envelope comprising front and back sheets 64 and 66, respectively, which conform in peripheral contour to front and back sheets 34 and 36. Sheets 64 and 66 are provided with openings corresponding to eye openings 58 and nose opening 60, and the sheets are heat sealed to front and back sheets 34 and 36 about the outer periphery thereof and about the latter openings and laterally extending lines 58b. As will be appreciated from FIG. 5, magnetic sheets 12, 14 and 16 are suitably secured between sheets 36 and 66 and, preferably, are adhesively bonded to the outer side of back sheet 66 of the envelope enclosing liquid 62. If the magnet sheet has the fabric covering 28 described above in connection with FIG. 3, such bonding provides for the fabric sheet to face the inner side of back sheet 36 of the face mask. This relationship precludes relative movement between the magnet sheets and back sheet 66 of the envelope which could cause wear of sheet 66 and potential puncturing thereof and thus leakage of liquid 62 from the envelope. Back sheet 36 of the face mask engages the face of a person wearing the mask, and the fabric layer on the magnet sheets promotes comfort for the wearer of the mask and protects back sheet 36 from being punctured by the peripheral edges of the magnet sheets.

In use, the mask is placed over a person's face and straps 46 and 48 are attached about the head using the VELCRO brand fastener components 52 and 54 at the ends thereof. The person wearing the mask then presses lightly on the front sheet 34 thereof to distribute liquid 62 within the pocket therefore so as to conform inner sheets 36 and 66 to the contour of the face and position the planar sides of the magnet sheets parallel to the surface portion of the face which they overly. As will be appreciated from FIG. 4, semi-circular magnet sheets 14 are provided in pairs on opposite sides of a corresponding one of the heat sealed lines 58b. This arrangement, including the laterally extending heat seal lines 58d promotes flexure of the mask about the heat sealed line to promote conforming the mask to the contour of a person's face such that the flat outer sides of the magnet sheets 14 are parallel to the temple portions of the face they overly. While the heat seal lines 58b could be eliminated and circular magnet sheets 12 could replace the semi-circular magnet sheets 14, the additional flexibility achieved with the arrangement shown is preferred. Preferably, to optimize such conforming of the mask to the facial contour and positioning of the magnet sheets relative to the face, liquid 62 has a viscous, creamy texture such that it can be moved in the pocket by squeezing while having sufficient body to remain in place in the pocket in the absence of such squeezing. A suitable liquid for this purpose is a cryolon gel prepared by mixing a liquid with a cellulose material available from Dow Chemical Company of Midland, Mich. under the latter's product designation Methocel. While such a viscous material is preferred, other liquids, including water, can be used.

Figure 3:
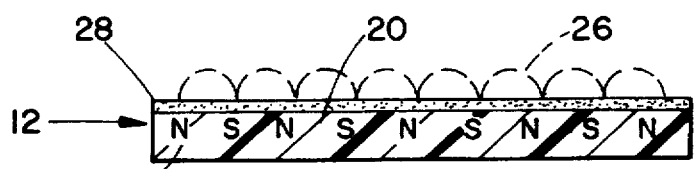
FIG. 3 is a cross-sectional view of the magnetic sheet material taken along line 3—3 in FIG. 2.

In the embodiment illustrated in FIG. 6 of the drawing, the face mask 10' includes only front and back sheets 34 and 36, and the pocket therebetween is provided with a filling 68 of thermoplastic sheet material similar to that used in the medical field for making dental forms and the like. In this respect, for example, the material can be a polymer composition which is normally rigid and which, when heated to a temperature of from about 120° F. to 160° F., becomes pliable and moldable and thus conformable to the contour of an underlying surface to which it applied. In conjunction with a face mask in accordance with the present invention, the mask is heated such as by immersion in hot water and then is positioned over the face of a person who is going to wear the mask and pressed thereagainst to conform with the contour of the underlying face portion. Upon cooling, filling 68 sets in the contour to which it was molded. A suitable material for this purpose is available from Tak Systems, Inc. of Wareham. Mass. under the latter's product designation Hydroplastic. As will be appreciated from the foregoing description regarding the embodiment in FIGS. 4 and 5, back sheet 36 of mask 10' engages against the wearer's face, whereby molding of the mask in the foregoing manner to conform with the contour of a wearer's face provides for back sheet 36 to conform with the latter contour and to position magnet sheets 12, 14 and 16 parallel to the underlying face portions. In this embodiment, magnet sheets 12, 14 and 16 are preferably supported on the inner side of back sheet 36 and in this respect, for example, can be adhesively bonded thereto. If the magnet sheets include the fabric layer 28 as shown in FIG. 3, the latter would face and be bonded to the inner side of back sheet 36. At the same, however, it will be appreciated that the magnet sheets could be bonded to the adjacent side of filler 68.

As an example of a face mask made in accordance with the foregoing embodiments, front and back sheets 34 and 36 and front and back envelope sheets 64 and 66 each have a thickness of from about 2 to 5 mils, and liquid filler 62, when evenly distributed throughout the pocket has a thickness of about 0.5 centimeters. Thermoplastic filling material 68 likewise has an unformed thickness of about 0.5 centimeters. Circular magnet sheets 12 from which magnets sheets 14 and 16 are constructed have a thickness of about 2 millimeters, a diameter of about 4 centimeters and a flux density of about 500 Gauss. While it is preferred as illustrated and described herein to support the magnet sheets adjacent the inner side of the back sheet of the mask, it will be appreciated that the magnet sheets could be attached to the outer side of the back sheet, or between front sheets 34 and 64 in the embodiment shown in FIG. 5, or on the outer side of sheet 34 in the latter embodiment, or on the inner or outer side of front sheet 34 in the embodiment shown in FIG. 6. Positioning of the magnet sheets toward the front side of the mask, such as on the inner side of front sheet 34, would necessitate increasing the flux density of the magnet to assure a desired penetration of the flux field inwardly of the surface of the face of a person wearing the mask.

It will be appreciated that while the preferred magnetic sheets described hereinabove are circular, or portions of a circle, and thus provide a preferred pattern of magnetization to promote the desired transverse relationship between the lines of flux and face wrinkles during use, other magnetic sheet material configurations as well as other patterns of magnetization can obviously be provided for this purpose. Likewise, while the magnetic sheet material preferably is flexible it can also be rigid.

While considerable emphasis has been placed on the preferred structures for a face mask in accordance with the present invention, it will be appreciated that the foregoing and other modifications of the preferred structures as well as other mask structures can be devised without departing from the invention, whereby it is to be distinctly understood that the foregoing descriptive matter is to be interpreted merely as illustrative of the invention and not as a limitation.

Having thus defined the invention, the following is claimed:

1. A face mask for applying a magnetic flux field to the face of a human being, said face mask having a peripheral edge and comprising front and back sheets of flexible material joined together to provide said peripheral edge, said back sheet being adapted to overlie a portion of the face of a person when said mask is applied to said face portion of said person, formable means between said front and back sheets and within said peripheral edge for conforming said back sheet to the contour of said face portion, and permanent magnetic means on said face mask contiguous with said back sheet for generating said magnetic flux field.

2. A face mask according to claim 1, wherein said permanent magnetic means comprises alternating north and south poles arranged to generate magnetic fields having angularities with respect to a line traversing said back sheet.

3. A face mask according to claim 2, wherein said formable means comprises a liquid and said magnetic means is positioned between said formable means and said back sheet.

4. A face mask according to claim 1, wherein said face portion comprises the forehead, temple and cheek areas of the face of said person, said face mask having areas overlying each of said areas of the face, and said permanent magnetic means comprising at least one permanent magnetic in each of said areas of said face mask.

5. A face mask according to claim 1, wherein said formable means comprises envelope means between said front and back sheets, said envelope means containing a viscous fluid.

6. A face mask according to claim 5, wherein said permanent magnetic means is positioned on said envelope means adjacent to said back sheet.

7. A face mask for applying a magnetic flux field to the face of a human being, said face mask having a peripheral edge and comprising a plurality of sheets of flexible material, said plurality of sheets including a front sheet and a back sheet joined together to provide said peripheral edge and a pocket therewithin, said back sheet being adapted to overlie a portion of the face of a person when said mask is applied to said face portion of said person, formable means in said pocket for conforming said back sheet to the contour of said face portion, and permanent magnetic means contiguous with said back sheet for generating said magnetic flux field.

8. A face mask according to claim 7, wherein said plurality of sheets of flexible material comprises a pair of sheets between said front and back sheets, said formable means in said pocket including said pair of sheets.

9. A face mask according to claim 8, wherein said formable means in said pocket comprises a liquid.

10. A face mask according to claim 9, wherein salad permanent magnetic means is adjacent said back sheet and said one of said pair of sheets.

11. A face mask according to claim 10, wherein said permanent magnetic means comprises a plurality of magnets.

12. A face mask according to claim 11, wherein said face portion includes the forehead, temple and cheek areas of the face of said person, said face mask having areas overlying each of said areas of the face, and said plurality of permanent magnets comprises at least one permanent magnet in each of said areas of said face mask.

13. A face mask according to claim 12, wherein each of said plurality of permanent magnets comprises alternating north and south poles arranged to generate magnetic fields having angularities with respect to a line traversing said back sheet.

14. A face mask according to claim 13, further comprising a strap means for removably supporting said face mask on said face portion.

15. A face mask according to claim 7, wherein said formable means in said pocket comprises thermoplastic material and said permanent magnet means is between said thermoplastic material and said back sheet.

16. A face mask according to claim 15, wherein said face portion comprises the forehead, temple, and cheek areas of the face of said person, said face mask having areas overlying each of said areas of the face, and said permanent magnetic means comprises at least one permanent magnet in each of said areas of said face mask.

17. A face mask according to claim 16, wherein said permanent magnetic means comprises alternating north and south poles arranged to generate magnetic fields having angularities with respect to a line traversing said back sheet.

18. A face mask according to claim 17, further comprising a strap means for removably supporting said face mask on said face portion.

19. Apparatus for applying a magnetic flux field to a body comprising front and rear flexible sheets sealed together at an edge and forming a pocket therebetween, one or more permanent magnets contiguous with said rear flexible sheet, and formable material in said pocket for allowing the configuration of said rear flexible sheet to vary selectively with respect to the configuration of said front flexible sheet whereby said rear flexible sheet is adapted to conform to the shape of said body.

* * * * *